(12) United States Patent
Xia et al.

(10) Patent No.: US 12,391,718 B2
(45) Date of Patent: Aug. 19, 2025

(54) POST-TREATMENT METHOD FOR SUCROSE-6-CARBOXYLATE CHLORINATION REACTION SOLUTION

(71) Applicant: ANHUI JINHE INDUSTRIAL CO., LTD., Anhui (CN)

(72) Inventors: Jiaxin Xia, Anhui (CN); Weiqiang Jiang, Anhui (CN); Zhengsong Zhang, Anhui (CN); Chaohui Chen, Anhui (CN); Qingyang Hu, Anhui (CN); Hao Zhang, Anhui (CN); Yang Wang, Anhui (CN)

(73) Assignee: ANHUI JINHE INDUSTRIAL CO., LTD., Anhui (CN)

( * ) Notice: Subject to any disclaimer, the term of this patent is extended or adjusted under 35 U.S.C. 154(b) by 486 days.

(21) Appl. No.: 18/003,350

(22) PCT Filed: Sep. 18, 2020

(86) PCT No.: PCT/CN2020/116202
§ 371 (c)(1),
(2) Date: Dec. 27, 2022

(87) PCT Pub. No.: WO2022/056840
PCT Pub. Date: Mar. 24, 2022

(65) Prior Publication Data
US 2023/0242564 A1    Aug. 3, 2023

(51) Int. Cl.
*C07H 13/08*    (2006.01)
*C07H 1/06*    (2006.01)

(52) U.S. Cl.
CPC ............... *C07H 13/08* (2013.01); *C07H 1/06* (2013.01)

(58) Field of Classification Search
CPC ....................................................... C07H 3/08
See application file for complete search history.

(56) References Cited

U.S. PATENT DOCUMENTS

2010/0168412 A1    7/2010  Ratnam et al.

FOREIGN PATENT DOCUMENTS

| CN | 101270136 A | 9/2008 |
|---|---|---|
| CN | 101472935 A | 7/2009 |
| CN | 108047283 A | 5/2018 |
| CN | 109956983 A | 7/2019 |
| CN | 110078189 A | 8/2019 |
| CN | 110938101 A | 3/2020 |
| CN | 111004131 A | 4/2020 |
| CN | 111548375 A | 8/2020 |

OTHER PUBLICATIONS

International Search Report and Written Opinion mailed Jun. 8, 2021, in connection with International Patent Application No. PCT/CN2020/116202, 9 pgs. (including translation).
First Office Action mailed Mar. 3, 2022, in connection with Chinese Patent Application No. 202080002543.0, 12 pgs. (including translation).
Second Office Action mailed Sep. 23, 2022, in connection with Chinese Patent Application No. 202080002543.0, 13 pgs. (including translation).
Rullyldice et al., "Optimization of Chlorination Reaction in Sucralose Production," 2018, "Chinese Food Additives", No. 11, pp. 49-55.

*Primary Examiner* — Layla D Berry
(74) *Attorney, Agent, or Firm* — Chiesa Shahinian & Giantomasi PC

(57) ABSTRACT

Provided is a post-treatment method for a sucrose-6-carboxylate chlorination reaction solution, including: adding ammonia water or water to the sucrose-6-carboxylate chlorination reaction solution to obtain a mixture, and subjecting the mixture to preliminary neutralization reaction; introducing an ammonia gas into a resulting reaction solution at a predetermined temperature, adjusting a pH of the resulting reaction solution to a predetermined alkalinity range, and conducting a reaction at a reaction temperature for a period of time; and adjusting a pH of a reaction solution obtained after the ammonia gas neutralization using an acid to a predetermined acidity range.

20 Claims, No Drawings

POST-TREATMENT METHOD FOR SUCROSE-6-CARBOXYLATE CHLORINATION REACTION SOLUTION

CROSS-REFERENCE TO RELATED APPLICATIONS

This application is a National Stage under 35 U.S.C. 371 of International Patent Application No. PCT/CN2020/116202, filed Sep. 18, 2020; the disclosure of which is incorporated herein by reference in its entirety.

TECHNICAL FIELD

The present disclosure relates to the technical field of fine chemical production, and in particular to a post-treatment method for a sucrose-6-carboxylate chlorination reaction solution.

BACKGROUND

Sucralose has high sweetness, prominent taste, and high safety, and thus has been widely used. It has no calories, and thus can be provided to obese patients, diabetic patients, cardiovascular disease (CVD) patients, and the elderly for use. Sucralose does not cause caries and can contribute to dental health.

Synthesis methods for sucralose include a hologroup-protected synthesis method and a monogroup-protected synthesis method. Among them, the hologroup-protected synthesis method can be implemented by a variety of production processes with high production cost, and is not suitable for mass production. The monogroup-protected synthesis method involves economical and easily available raw materials, high selectivity, and simple production processes, and is commonly used for production in the prior art. For the monogroup-protected synthesis method, a chlorination reaction is a key step: chlorination reaction intermediates exist in a resulting solution of the chlorination reaction, and therefore a neutralization for the resulting solution is very important for improvement of a yield and purity of trichlorosucralose-6-acetate.

A chlorination reaction is a key for the monogroup-protected synthesis method. During the chlorination reaction, due to the use of strong chlorinating agents such as thionyl chloride and carbonyl chloride in the reaction solution, and the high temperature during the chlorination holding phase, by-products such as monochlorosucrose-6-esters, dichlorosucrose-6-esters, and tetrachlorosucrose-6-esters are produced. Therefore, after the end of the chlorination holding phase, how to improve a yield and purity of sucralose-6-acetate in the reaction solution is very important.

At present, for the neutralization of chlorination reaction solution in large-scale production inside and outside China, alkaline solutions such as ammonia water and sodium hydroxide are generally used, and an ammonia gas can also be used directly in a few reports. The neutralization using alkaline solutions such as ammonia water and sodium hydroxide can cause a side reaction of hydrolysis, resulting in a reduced sucralose-6-ester yield; due to the presence of a large amount of water in the reaction solution, an organic solvent obtained after subsequent concentration needs to undergo dehydration for recycling; and after the dehydration of the organic solvent, a large amount of wastewater is generated and can only be discharged after a recovery treatment, which increases a recovery cost. The neutralization directly using an ammonia gas (Chinese patent application CN 108047283A) can lead to a waste of the ammonia gas because the ammonia gas has a low absorption efficiency in a system as a result of low solubility. In addition, the neutralization directly using an ammonia gas can make alkaline hydrolysis of an intermediate for a chlorination reaction be carried out under anhydrous conditions, such that the reaction is slow, a progress of which is difficult to be controlled, resulting in an inadequate reaction easily, which reduces a yield of a sucralose-6-carboxylate.

SUMMARY

In view of the above, a post-treatment method for a sucrose-6-carboxylate chlorination reaction solution is provided in the present disclosure to overcome the above problems or at least partially solve the above problems.

According to an aspect of the present disclosure, provided is a post-treatment method for a sucrose-6-carboxylate chlorination reaction solution, including:

preliminary neutralization: adding ammonia water or water to the sucrose-6-carboxylate chlorination reaction solution to obtain a mixture, and subjecting the mixture to preliminary neutralization reaction;

ammonia gas neutralization: introducing an ammonia gas into a reaction solution obtained after the preliminary neutralization at a predetermined temperature, adjusting a pH to a predetermined alkalinity range, and conducting a reaction at a reaction temperature for a predetermined reaction time; and acid value adjustment: adjusting a pH of a reaction solution obtained after the ammonia gas neutralization using an acid to a predetermined acidity range to obtain a neutralized reaction solution.

The present disclosure has the following beneficial effects:

1. In the present disclosure, a small amount of ammonia water or water is first added to the sucrose-6-carboxylate chlorination reaction solution, which can effectively increase the absorption efficiency of the ammonia gas in the subsequent steps so as to improve the utilization of the ammonia gas.

2. Under the condition that the reaction solution includes a small amount of water, the ammonia gas is introduced into the reaction solution for neutralization, which avoids the generation of side reactions of sucrose-6-ester hydrolysis so as to improve the conversion and selectivity of the reaction.

3. Since the reaction solution includes a small amount of water, after the neutralization, an organic solvent subsequently recovered by distillation can be directly recycled in the next batch of chlorination reactions only after a simple treatment, which reduces the cumbersome procedure that a recovered organic solvent needs to undergo dehydration distillation in the prior art, and avoids the generation of a large amount of wastewater and the wastewater treatment, greatly reducing the production cost.

The above description is merely a summary of the technical solutions of the present disclosure. In order to allow the technical means of the present disclosure to be understood clearly and implemented in accordance with the content of the specification and allow the above and other objects, features, and advantages of the present disclosure to be clear and easy to be understood, embodiments of the present disclosure are described below.

DETAILED DESCRIPTION OF THE EMBODIMENTS

Exemplary embodiments of the present disclosure will be described in detail below. It should be appreciated that the present disclosure can be implemented in various forms and should not be limited to the embodiments described herein. Instead, these embodiments are provided to enable the present disclosure to be more thoroughly understood and to enable the scope of the present disclosure to be fully conveyed to those skilled in the art.

The concept of the present disclosure is as follows: The inventors find that the pretreatment of the sucrose-6-carboxylate chlorination reaction solution using ammonia water or water allows for improvement of the absorption of ammonia gas by the sucrose-6-carboxylate chlorination reaction solution in the subsequent steps. Based on this discovery, in the present disclosure the sucrose-6-carboxylate chlorination reaction solution is first preliminarily neutralized using ammonia water or a small amount of water, and then neutralized using an ammonia gas, which could not only avoid the side reactions of hydrolysis of sucralose-6-acetate under alkaline conditions during ammonia water neutralization in the traditional technology, but also avoid the problems of poor absorption effect and insufficient reaction during neutralization using ammonia gas alone.

The present disclosure provides a post-treatment method for a sucrose-6-carboxylate chlorination reaction solution, which comprises the following steps:

Preliminary neutralization, adding ammonia water or water to the sucrose-6-carboxylate chlorination reaction solution to obtain a mixture, and subjecting the mixture to preliminary neutralization reaction.

The sucrose-6-carboxylate chlorination reaction solution in the present disclosure refers to a reaction mixed solution obtained after a chlorination holding reaction of sucrose-6-carboxylate and a chlorinating agent. The present disclosure is applicable to reaction solutions produced in a chlorination reaction phase during the preparation of sucralose by various methods in the prior art, such as a monogroup-protected synthesis method and a multigroup-protected synthesis method. In the present disclosure, there is no restriction on the source of the sucrose-6-carboxylate chlorination reaction solution, and a reaction solution produced in a chlorination reaction phase during the preparation of sucralose in the laboratory or industrial production may be used.

Because the use of strong chlorinating agents such as thionyl chloride and carbonyl chloride during the chlorination reaction process and the high temperature during a chlorination holding phase, a series of by-products may be produced, such as monochlorosucrose-6-carboxylate, dichlorosucrose-6-carboxylate, and tetrachlorosucrose-6-carboxylate. At present, in the prior art, the sucrose-6-carboxylate chlorination reaction solution is generally neutralized using sodium hydroxide or ammonia water or directly using an ammonia gas, but a product sucralose-6-carboxylate is in an alkaline solution, which will cause a hydrolysis reaction of sucralose-6-carboxylate to produce by-products, thereby reducing a yield of sucralose-6-carboxylate.

In the present disclosure, when a sucrose-6-carboxylate chlorination reaction solution is neutralized, it is found that a small amount of ammonia water or water is first added for preliminary neutralization, which can improve the absorption of ammonia gas by the reaction solution in the subsequent steps. Thus, the post-treatment method provided by the present disclosure can increase a yield of sucralose-6-carboxylate, avoid the trouble that a large amount of wastewater has to be treated subsequently, and ensure that an organic solvent in the reaction solution can be separated by concentration and then directly recycled, which simplifies the operation and greatly reduces the production cost.

Ammonia gas neutralization: introducing an ammonia gas into a reaction solution obtained after the preliminary neutralization at a predetermined temperature, adjusting a pH of the reaction solution to a predetermined alkalinity range, and conducting a reaction at a reaction temperature for a predetermined reaction time.

After the preliminary treatment of the sucrose-6-carboxylate chlorination reaction solution using ammonia water or water, a pH of the reaction solution is adjusted using an ammonia gas to a predetermined alkalinity range at a predetermined temperature, and then a reaction is conducted at a reaction temperature for a period of time (namely, a predetermined reaction time).

In the present disclosure, the pH is first adjusted using an alkaline substance to the predetermined alkalinity range, because a chlorination product in the sucrose-6-carboxylate chlorination reaction solution can be hydrolyzed into a target product only when the pH is in the predetermined alkalinity range. It should be noted that the predetermined alkalinity range is a descriptive phrase, which does not refer to an absolute alkalinity range and may be considered as an alkalinity range close to neutrality in the present disclosure.

Acid value adjustment: adjusting a pH of a reaction solution obtained after the ammonia gas neutralization using an acid to a predetermined acidity range to obtain a neutralized reaction solution.

After the sucrose-6-carboxylate chlorination reaction solution is subjected to a reaction for a predetermined time under alkaline conditions, the pH of the resulting reaction solution is adjusted using the acid to the predetermined acidity range. It should be noted that the predetermined acidity range is a descriptive phrase, which does not refer to an absolute acidity range and may be considered as an acidity range close to neutrality in the present disclosure.

The pH of the sucrose-6-carboxylate chlorination reaction solution is adjusted to the predetermined acidity range, because it allows the side reactions to be avoided.

Amount of Ammonia Water or Water

In the present disclosure, there is no restriction on the amount of the ammonia water or water in the preliminary neutralization. In some embodiments of the present disclosure, a molar ratio of the ammonia water or water to the sucrose-6-carboxylate is in a range of 0.2 to 5; and in some other embodiments, the molar ratio is in a range of 0.5 to 2.5. If the amount of the ammonia water or water is less than 0.2 times an amount of the sucrose-6-carboxylate, it indicates that the amount is too small, which leads to a decreased absorption efficiency and a poor reaction effect; and if the amount of the ammonia water or water is greater than 5 times the amount of the sucrose-6-carboxylate, it indicates that the amount is too much, which leads to a formation of two phases easily and high pH of local components resulting in the increase of side reactions, which is unfavorable for the reaction.

Amount of Ammonia Gas

In the present disclosure, there is no restriction on the amount and the flow rate of the ammonia gas in the ammonia gas neutralization. In some embodiments of the present disclosure, a molar ratio of the ammonia gas to the sucrose-6-carboxylate is in a range of 0.5 to 10; and in some other embodiments, the molar ratio is in a range of 2.0 to 6.0. In addition, the flow rate of the ammonia gas can be determined according to the amount of the ammonia gas and an introduction time of the ammonia gas. If the amount of the ammonia gas is less than 0.5 times the molar amount of the sucrose-6-carboxylate, it indicates that the amount of the ammonia gas is too small, and the expected neutralization effect cannot be achieved; and if the amount of the ammonia gas is greater than 10 times the molar amount of the sucrose-6-carboxylate, it indicates that the amount of the ammonia gas is too much, and the pH may exceed the expected predetermined alkalinity range.

In the prior art, during the neutralization of the sucrose-6-ester chlorination reaction solution directly using an ammonia gas, the amount of the ammonia gas is about 12 times or more the molar amount of the sucrose-6-carboxylate. While in the present disclosure, a molar ratio of the ammonia gas to the sucrose-6-carboxylate is in a range of 0.5 to 10, resulting in that the consumption of the ammonia gas can be reduced greatly.

Conditions for Ammonia Gas Introduction

In the present disclosure, there is no restriction on the conditions for ammonia gas introduction in the ammonia gas neutralization. In some embodiments, the predetermined temperature may be in a range of 30° C. to 95° C.; and in some other embodiments, the predetermined temperature may be in a range of 40° C. to 70° C. If the ammonia gas is introduced at a temperature lower than 30° C., the introduction conditions are too mild, the neutralization reaction is too slow, and the possibility of side reactions to be occurred is increased so as to generate by-products. If the ammonia gas is introduced at a temperature higher than 95° C., the reaction conditions are too intense, and the neutralization reaction is too fast. In addition, because the neutralization reaction is an exothermic reaction, the too-high temperature even causes local bumping of the reaction solution.

In some embodiments of the present disclosure, in the ammonia gas neutralization, the reaction solution is neutralized using an ammonia gas to be weakly alkaline; and when the pH of the reaction solution is adjusted to the predetermined alkalinity range, the ammonia gas is stopped from being introduced. In some embodiments, the predetermined alkalinity range is in a range of 7.5 to 9.0; and in some other embodiments, the predetermined alkalinity range is in a range of 8.0 to 8.5. In this step, if the pH is lower than 7.5, the neutralization reaction will be insufficient, such that the chlorination intermediate cannot be completely hydrolyzed. If the pH is higher than 9.0, side reactions such as acetyl degradation are easy to occur, resulting in a decreased yield.

Conditions for Ammonia Gas Neutralization

In some embodiments of the present disclosure, there is no restriction on the reaction conditions in the ammonia gas neutralization. In some embodiments, the ammonia gas neutralization is conducted at a temperature of 10° C. to 80° C. for 0.5 h to 12 h; and in some other embodiments, the ammonia gas neutralization is conducted at a temperature of 20° C. to 50° C. for 2 h to 6 h. If the ammonia gas neutralization is conducted at a temperature lower than 10° C., the reaction conditions are too mild, the neutralization reaction is too slow, and the chlorination intermediate cannot be completely decomposed, thereby affecting the yield; and if the ammonia gas neutralization is conducted at a temperature higher than 80° C., the reaction conditions are too intense, and the neutralization reaction is too fast. In addition, because the neutralization reaction is an exothermic reaction, the too-high temperature even causes side reactions such as degradation and ammonolysis. If the ammonia gas neutralization is conducted for less than 0.5 h, the reaction time is too short, and the neutralization reaction will be incomplete; and if the ammonia gas neutralization is conducted for more than 12 h, the reaction time is too long, and the neutralization reaction has been completed, so that there is no need to prolong the reaction time, because a too-long time is easy to cause the alkaline hydrolysis of sucrose-6-carboxylate.

Conditions for Acid Value Adjustment

In the acid value adjustment, the pH of the reaction solution is adjusted using an acid to the predetermined acidity range. In some embodiments of the present disclosure, the predetermined acidity range is in a range of 4.0 to 7.5; and in some other embodiments, the predetermined acidity range is in a range of 5.5 to 7.0. If the predetermined acidity range is lower than 4.0, a resulting neutralized reaction solution has a too-high acidity, which leads to the decomposition of saccharides; and if the predetermined acidity range is higher than 7.5, a resulting neutralized reaction solution has a too-high alkalinity, which easily leads to side reactions such as acetyl degradation and results in a decreased yield.

Acid Types

In the present disclosure, there is no restriction on the types of the acid used in the acid value adjustment. In some embodiments, the acid is hydrochloric acid or acetic acid; and in some other embodiments, the acid is hydrochloric acid. The acid can be used directly or can be used after mixing with water.

In some embodiments of the present disclosure, the post-treatment method further includes: purification: concentrating the neutralized reaction solution by evaporation to obtain a slurry and an organic solvent; dissolving the slurry in water, and removing a carbon residue by suction filtration to obtain a sucralose-6-carboxylate aqueous solution; and subjecting the organic solvent to azeotropic dehydration for recycling.

In some embodiments of the present disclosure, the post-treatment method further includes: crystallization: adding an extraction solvent to the sucralose-6-carboxylate aqueous solution at an extraction temperature, and conducting extraction on the sucralose-6-carboxylate aqueous solution, and cooling to obtain a sucralose-6-carboxylate crystal. In some embodiments of the present disclosure, the extraction solvent is any one selected from the group consisting of ethyl acetate, propyl acetate, toluene, and butyl acetate; and in some other embodiments, the extraction solvent is ethyl acetate. The extraction temperature is a temperature commonly used in the art, such as 40° C. to 60° C.

Due to the high polarity of the sucralose-6-ester, the solubility of the sucralose-6-ester in water is much higher than that of the sucralose-6-ester in any one selected from the group consisting of ethyl acetate, propyl acetate, toluene, and butyl acetate; impurities in a sucralose-6-ester crude product obtained after a chlorination reaction are mostly species with low polarity. It has been found that the extraction using the above solvents for the sucralose-6-ester crude product can selectively remove a variety of impurities to achieve a good purification effect, and in particular a prominent effect for ethyl acetate.

Example 1

A post-treatment method of a sucrose-6-carboxylate chlorination reaction solution in sucralose production was provided in this example, which was conducted as follows:

S1: 35 mL of 20 wt % ammonia water was added dropwise to 1,000 mL of a sucrose-6-acetate chlorination reaction solution at room temperature under stirring to obtain a preliminarily-neutralized reaction solution. The preliminarily-neutralized reaction solution was heated to 40° C. Then an ammonia gas was introduced at a flow rate of 250 mL/min for neutralization. The neutralization was conducted at about 50° C. for 2 h until a resulting reaction solution had a pH of about 8.5. Then the reaction solution continued to be reacted under stirring for another 4 h. After that, a pH of are suiting reaction solution was adjusted with acetic acid to 6.0 to 7.0 to obtain a neutralized reaction solution.

S2: The neutralized reaction solution obtained in S1 was subjected to rotary evaporation at a temperature of 70° C. to 80° C. to remove the solvent. A residue was dissolved with 500 mL of water, and a carbon residue was removed by suction filtration to obtain a treated sucralose-6-acetate aqueous solution.

S3: 200 mL of ethyl acetate was added to the treated sucralose-6-acetate aqueous solution obtained in S2, and a resulting mixture was cooled for crystallization to obtain a crude sucralose-6-acetate solid. After conversing into purification, the sucralose-6-acetate had a mass of 55 g, namely, there are 55 g of the sucralose-6-acetate per 100 g of the crude sucralose-6-acetate solid.

In this example, a water content in an organic solvent separated by rotary evaporation was about 0.5 wt %. The separated organic solvent was then subjected to azeotropic distillation until a mass of a resulting organic solvent was 90% of the total mass of the separated organic solvent, such that a water content in the organic solvent reached 0.05 wt % or lower, which complied with the recycling standards.

Example 2

A post-treatment method of a sucrose-6-carboxylate chlorination reaction solution in sucralose production was provided in this example, which was conducted as follows:

S1: 30 mL of water was added dropwise to 1,000 mL of a sucrose-6-acetate chlorination reaction solution at room temperature under stirring to obtain a preliminarily-neutralized reaction solution. The preliminarily-neutralized reaction solution was heated to 30° C. Then an ammonia gas was introduced at a controlled flow rate for neutralization. The neutralization was conducted at about 40° C. for 3 h until a resulting reaction solution had a pH of about 8.0. Then the reaction solution continued to be reacted under stirring for another 4 h. After that, a pH of a resulting reaction solution was adjusted with acetic acid to 6.0 to 7.0 to obtain a neutralized reaction solution.

S2: The neutralized reaction solution obtained in S1 was subjected to rotary evaporation at a temperature of 70° C. to 80° C. to remove the solvent. A residue was dissolved with 500 mL of water, and a carbon residue was removed by suction filtration to obtain a treated sucralose-6-acetate aqueous solution.

S3: 200 mL of ethyl acetate was added to the treated sucralose-6-acetate aqueous solution obtained in S2, and a resulting mixture was cooled for crystallization to obtain a crude sucralose-6-acetate solid. After conversing into purification, the sucralose-6-acetate had a mass of 52 g, namely, there are 52 g of the sucralose-6-acetate per 100 g of the crude sucralose-6-acetate solid.

In this example, a water content in an organic solvent separated by rotary evaporation was about 0.4 wt %. The separated organic solvent was then subjected to azeotropic distillation until a mass of a resulting organic solvent was 90% of the total mass of the separated organic solvent, such that a water content in the organic solvent reached 0.05 wt % or lower, which complied with the recycling standards.

Example 3

A post-treatment method of a sucrose-6-carboxylate chlorination reaction solution in sucralose production was provided in this example, which was conducted as follow:

S1: 40 mL of 20 wt % ammonia water was added dropwise to 1,000 mL of a sucrose-6-acetate chlorination reaction solution at room temperature under stirring to obtain a preliminarily-neutralized reaction solution. The preliminarily-neutralized reaction solution was heated to 40° C. Then an ammonia gas was introduced at a controlled flow rate for neutralization. The neutralization was conducted at about 70° C. for 2 h until a resulting reaction solution had a pH of about 8.3. Then the reaction solution continued to be reacted under stirring for another 4 h. After that, a pH of a resulting reaction solution was adjusted with hydrochloric acid to 6.0 to 7.0 to obtain a neutralized reaction solution.

S2: The neutralized reaction solution obtained in S1 was subjected to rotary evaporation at a temperature of 70° C. to 80° C. to remove the solvent. A residue was dissolved with 500 mL of water, and a carbon residue was removed by suction filtration to obtain a treated sucralose-6-acetate aqueous solution.

S3: 200 mL of ethyl acetate was added to the treated sucralose-6-acetate aqueous solution obtained in S2, and a resulting mixture was cooled for crystallization to obtain a crude sucralose-6-acetate solid. After conversing into purification, the sucralose-6-acetate had a mass of 53 g, namely, there are 53 g of the sucralose-6-acetate per 100 g of the crude sucralose-6-acetate solid.

In this example, a water content in an organic solvent separated by rotary evaporation was about 0.9 wt %. The separated organic solvent was then subjected to azeotropic distillation until a mass of a resulting organic solvent was 85% of the total mass of the separated organic solvent, such that a water content in the organic solvent reached 0.05 wt % or lower, which complied with the recycling standards.

Example 4

A post-treatment method of a sucrose-6-carboxylate chlorination reaction solution in sucralose production was provided in this example, which was conducted as follow:

S1: 35 mL of 20 wt % ammonia water was added dropwise to 1,000 mL of a sucrose-6-acetate chlorination reaction solution at room temperature under stirring to obtain a preliminarily-neutralized reaction solution. The preliminarily-neutralized reaction solution was heated to 40° C. Then an ammonia gas was introduced at a flow rate of 250 mL/min for neutralization. The neutralization was conducted at about 75° C. for 2 h until a resulting reaction solution had a pH of about 8.5. Then the reaction solution continued to be reacted under stirring for another 4 h. After that, a pH of a resulting reaction solution was adjusted with acetic acid to 6.0 to 7.0 to obtain a neutralized reaction solution.

S2: The neutralized reaction solution obtained in S1 was subjected to rotary evaporation at a temperature of 70° C. to 80° C. to remove the solvent. A residue was dissolved with 500 mL of water, and a carbon residue was removed by suction filtration to obtain a treated sucralose-6-acetate aqueous solution.

S3: 200 mL of ethyl acetate was added to the treated sucralose-6-acetate aqueous solution obtained in S2, and a resulting mixture was cooled for crystallization to obtain a crude sucralose-6-acetate solid. After conversing into purification, the sucralose-6-acetate had a mass of 51 g, namely, there are 51 g of the sucralose-6-acetate per 100 g of the crude sucralose-6-acetate solid.

In this example, a water content in an organic solvent separated by rotary evaporation was about 0.5 wt %. The separated organic solvent was then subjected to azeotropic distillation until a mass of a resulting organic solvent was 90% of the total mass of the separated organic solvent, such that a water content in the organic solvent reached 0.05 wt % or lower, which complied with the recycling standards.

Example 5

A post-treatment method of a sucrose-6-carboxylate chlorination reaction solution in sucralose production was provided in this example, which was conducted as follows:

S1: 33 mL of water was added dropwise to 1,000 mL of a sucrose-6-acetate chlorination reaction solution at room temperature under stirring to obtain a preliminarily-neutralized reaction solution. The preliminarily-neutralized reaction solution was heated to 50° C. Then an ammonia gas was introduced at a controlled flow rate for neutralization. The neutralization was conducted at about 55° C. for 3 h until a resulting reaction solution had a pH of about 8.0. Then the reaction solution continued to be reacted under stirring for another 4 h. After that, a pH of a resulting reaction solution was adjusted with acetic acid to 6.0 to 7.0 to obtain a neutralized reaction solution.

S2: The neutralized reaction solution obtained in S1 was subjected to rotary evaporation at a temperature of 70° C. to 80° C. to remove the solvent. A residue was dissolved with 500 mL of water, and a carbon residue was removed by suction filtration to obtain a treated sucralose-6-acetate aqueous solution.

S3: 200 mL of ethyl acetate was added to the treated sucralose-6-acetate aqueous solution obtained in S2, and a resulting mixture was cooled for crystallization to obtain a crude sucralose-6-acetate solid. After conversing into purification the sucralose-6-acetate had a mass of 53 g, namely, there are 53 g of the sucralose-6-acetate per 100 g of the crude sucralose-6-acetate solid.

In this example, a water content in an organic solvent separated by rotary evaporation was about 0.5 wt %. The separated organic solvent was then subjected to azeotropic distillation until a mass of a resulting organic solvent was 90% of the total mass of the separated organic solvent, such that a water content in the organic solvent reached 0.05 wt % or lower, which complied with the recycling standards.

Example 6

A post-treatment method of a sucrose-6-carboxylate chlorination reaction solution in sucralose production was provided in this example, which was conducted as follows:

S1: 30 mL of water was added dropwise to 1,000 mL of a sucrose-6-benzoate chlorination reaction solution at room temperature under stirring to obtain a preliminarily-neutralized reaction solution. The preliminarily-neutralized reaction solution was heated to 40° C. Then an ammonia gas was introduced at a controlled flow rate for neutralization. The neutralization was conducted at about 50° C. for 3 h until a resulting reaction solution had a pH of about 8.5. Then the reaction solution continued to be reacted under stirring for another 4 h. After that a pH of a resulting reaction solution was adjusted with hydrochloric acid to 6.0 to 7.0 to obtain a neutralized reaction solution.

S2: The neutralized reaction solution obtained in S1 was subjected to rotary evaporation at a temperature of 70° C. to 80° C. to remove the solvent. A residue was dissolved with 500 mL of water, and a carbon residue was removed by suction filtration to obtain a treated sucralose-6-benzoate aqueous solution.

S3: 300 mL of ethyl acetate was added to the treated sucralose-6-acetate aqueous solution obtained in S2 and then subjected to extraction. After the extraction, recrystallization was conducted in methanol to obtain a crude sucralose-6-benzoate solid. After conversing into purification, the sucralose-6-benzoate had a mass of 55 g, namely, there are 55 g of the sucralose-6-benzoateper 100 g of the crude sucralose-6-benzoate solid.

In this example, a water content in an organic solvent separated by rotary evaporation was about 0.5 wt %. The separated organic solvent was then subjected to azeotropic distillation until a mass of a resulting organic solvent was 90% of the total mass of the separated organic solvent, such that a water content in the organic solvent reached 0.05 wt % or lower, which complied with the recycling standards.

Example 7

A post-treatment method of a sucrose-6-carboxylate chlorination reaction solution in sucralose production was provided in this example, which was conducted as follows:

S1: 36 mL of water was added dropwise to 1.000 mL of a sucrose-6-benzoate chlorination reaction solution at room temperature under stirring to obtain a preliminarily-neutralized reaction solution. The preliminarily-neutralized reaction solution was heated to 50° C. Then an ammonia gas was introduced at a controlled flow rate for neutralization. The neutralization was conducted at about 70° C. for 3 h until a resulting reaction solution had a pH of about 8.5. Then the reaction solution continued to be reacted under stirring for another 4 h. After that a pH of a resulting reaction solution was adjusted with hydrochloric acid to 6.0 to 7.0 to obtain a neutralized reaction solution.

S2: The neutralized reaction solution obtained in S1 was subjected to rotary evaporation at a temperature of 70° C. to 80° C. to remove the solvent. A residue was dissolved with 500 mL of water, and a carbon residue was removed by suction filtration to obtain a treated sucralose-6-benzoate aqueous solution.

S3: 300 mL of ethyl acetate was added to the treated sucralose-6-benzoate aqueous solution obtained in S2 and then subjected to extraction. After the extraction, recrystallization was conducted in methanol to obtain a crude sucralose-6-benzoate solid. After conversing into purification, the sucralose-6-benzoate had a mass of 53 g, namely, there are 53 g of the sucralose-6-benzoate per 100 g of the crude sucralose-6-benzoate solid.

In this example, a water content in an organic solvent separated by rotary evaporation was about 0.6 wt %. The separated organic solvent was then subjected to azeotropic distillation until a mass of a resulting organic solvent was 85% of the total mass of the separated organic solvent, such that a water content in the organic solvent reached 0.05 wt % or lower, which complied with the recycling standards.

Comparative Example 1

In Comparative Example 1, a sucrose-6-acetate chlorination reaction solution was neutralized with a pure ammonia gas. The method was conducted as follows:

S1: 1,000 mL of the sucrose-6-acetate chlorination reaction solution was stirred at room temperature and then cooled, and then an ammonia gas was introduced at 25° C.

for neutralization. The neutralization was conducted at this temperature in a water bath until a resulting reaction solution had a pH of about 9, which took about 4 h. After that, the pH of a resulting reaction solution was adjusted with acetic acid to 6 to 7.

S2: A neutralized reaction solution obtained in S1 was subjected to rotary evaporation at a temperature of 70° C. to 80° C. to remove the solvent to obtain a slurry. The slurry was dissolved with 500 mL of water, and a carbon residue was removed by suction filtration to obtain a treated sucralose-6-acetate aqueous solution.

S3: 200 mL of ethyl acetate was added to the treated sucralose-6-acetate aqueous solution, and a resulting mixture was cooled for crystallization to obtain a crude sucralose-6-acetate solid. After conversing into purification, the sucralose-6-acetate had a mass of 48 g, namely, there are 48 g of the sucralose-6-acetate per 100 g of the crude sucralose-6-acetate solid.

In this comparative example, a water content in a distilled organic solvent was 0.08% or lower, which complied with the recycling standards.

Comparative Example 2

In Comparative Example 2, a sucrose-6-acetate chlorination reaction solution was neutralized with a pure ammonia gas. The method was conducted as follows:

S1: 1,000 mL of the sucrose-6-acetate chlorination reaction solution was stirred at room temperature and then cooled, and then an ammonia gas was introduced at 50° C. for neutralization. The neutralization was conducted at this temperature in a water bath until a resulting reaction solution had a pH of about 9; and then the pH of a resulting reaction solution was adjusted with acetic acid to 6 to 7.

S2: A neutralized reaction solution obtained in S1 was subjected to rotary evaporation at a temperature of 70° C. to 80° C. to remove the solvent to obtain a slurry. The slurry was dissolved with 500 mL of water, and a carbon residue was removed by suction filtration to obtain a treated sucralose-6-acetate aqueous solution.

S3: 200 mL of ethyl acetate was added to the treated sucralose-6-acetate aqueous solution, and a resulting mixture was cooled for crystallization to obtain a crude sucralose-6-acetate solid. After conversing into purification, the sucralose-6-acetate had a mass of 49 g, namely, there are 49 g of the sucralose-6-acetate per 100 g of the crude sucralose-6-acetate solid. In this comparative example, a water content in a distilled organic solvent was 0.08% or lower, which complied with the recycling standards.

Comparative Example 3

In Comparative Example 3, a sucrose-6-acetate chlorination reaction solution was neutralized with ammonia water. The method was conducted as follows:

S1: 1,000 mL of the sucrose-6-acetate chlorination reaction solution was stirred and then cooled, and then 180 mL of ammonia water was slowly added dropwise at 10° C. for neutralization. The neutralization was conducted at this temperature until a resulting reaction solution had a pH of about 9; and the reaction solution was stirred for another 1 h. After that, a pH of the reaction solution was adjusted with hydrochloric acid to 6 to 7.

S2: A neutralized reaction solution obtained in S1 was subjected to suction filtration to remove the carbon residue and salt, a filtrate was subjected to rotary evaporation at a temperature of 70° C. to 80° C. to remove the solvent to obtain a slurry, and the slurry was dissolved with 500 mL of water to obtain a treated sucralose-6-acetate aqueous solution.

S3: 200 mL of ethyl acetate was added to the treated sucralose-6-acetate aqueous solution, and a resulting mixture was cooled for crystallization to obtain a crude sucralose-6-acetate solid. After conversing into purification, the sucralose-6-acetate had a mass of 50 g, namely, there are 50 g of the sucralose-6-acetate per 100 g of the crude sucralose-6-acetate solid. In this comparative example, a mixture of water and an organic solvent was distilled out, which cannot be recycled.

It can be seen from Examples 1 to 7 and Comparative Examples 1 to 3 that the addition of a small amount of ammonia water or water to the sucrose-6-carboxylate chlorination reaction solution can effectively increase the absorption efficiency of the ammonia gas in subsequent steps to improve the utilization of the ammonia gas and avoid the generation of sucrose-6-ester hydrolysis side reactions to improve the conversion and selectivity of the reaction; and the recovery of an organic solvent by distillation thereafter can reduce the cumbersome procedures in the prior art, avoid the generation of a large amount of wastewater and the wastewater treatment, and greatly reduce the production cost.

In summary, the present disclosure has the following beneficial effects:

1. In the present disclosure, a small amount of ammonia water or water is first added to the sucrose-6-carboxylate chlorination reaction solution, which can effectively increase the absorption efficiency of the ammonia gas in the subsequent steps to improve the utilization of the ammonia gas.

2. Under the condition that the reaction solution includes a small amount of water, the ammonia gas is introduced into the reaction solution for neutralization, which avoids the generation of side reactions of sucrose-6-carboxylate hydrolysis so as to improve the conversion and selectivity of the reaction.

3. Since the reaction solution includes a small amount of water, after the neutralization, an organic solvent subsequently recovered by distillation can be directly recycled in the next batch of chlorination reactions only after a simple treatment, which reduces the cumbersome procedure that a recovered organic solvent needs to undergo dehydration distillation in the prior art, and avoids the generation of a large amount of wastewater and the wastewater treatment, greatly reducing the production cost.

The above are merely specific embodiments of the present disclosure, and under the above instruction of the present disclosure, those skilled in the art can make other improvements or variations on the basis of the above examples. Those skilled in the art should understand that the above specific description is merely intended to well explain the purpose of the present disclosure, and a protection scope of the present disclosure shall be subject to the protection scope of the claims.

In addition, those skilled in the art could understand that, although some embodiments herein include some features included in other embodiments but no other features, a combination of features of different examples falls within the scope of the present disclosure and forms a different embodiment. For example, in the claims, any one of the claimed embodiments could be used in any combination.

What is claimed is:

1. A post-treatment method for a sucrose-6-carboxylate chlorination reaction solution, comprising:
adding ammonia water or water to the sucrose-6-carboxylate chlorination reaction solution to obtain a mixture, and subjecting the mixture to a preliminary neutralization reaction;
introducing an ammonia gas into a reaction solution obtained after the preliminary neutralization at a predetermined temperature, adjusting a pH of the reaction solution to a predetermined alkalinity range, and conducting an ammonia gas neutralization reaction at a reaction temperature for a predetermined reaction time; and
adjusting, in an acid value adjustment reaction, a pH of a reaction solution obtained after the ammonia gas neutralization using an acid to a predetermined acidity range, to obtain a neutralized reaction solution.

2. The post-treatment method according to claim 1, further comprising:
concentrating the neutralized reaction solution by evaporation to obtain a slurry and an organic solvent; dissolving the slurry in water, and removing a carbon residue by suction filtration to obtain a sucralose-6-carboxylate aqueous solution; and subjecting the organic solvent to azeotropic dehydration for recycling.

3. The post-treatment method according to claim 2, further comprising:
adding an extraction solvent to the sucralose-6-carboxylate aqueous solution at an extraction temperature, and conducting extraction on the sucralose-6-carboxylate aqueous solution, and cooling to obtain a sucralose-6-carboxylate crystal.

4. The post-treatment method according to claim 3, wherein the extraction solvent is any one selected from the group consisting of ethyl acetate, propyl acetate, toluene, and butyl acetate.

5. The post-treatment method according to claim 1, wherein in the preliminary neutralization reaction, a molar ratio of the ammonia water or the water to the sucrose-6-carboxylate is in a range of 0.2 to 5.

6. The post-treatment method according to claim 1, wherein in the ammonia gas neutralization reaction, the predetermined temperature is in a range of 30° C. to 95° C.; and
the predetermined alkalinity range is in a range of 7.5 to 9.0.

7. The post-treatment method according to claim 1, wherein in the ammonia gas neutralization reaction, the reaction temperature is in a range of 10° C. to 80° C.; and
the predetermined reaction time is in a range of 0.5 h to 12 h.

8. The post-treatment method according to claim 1, wherein in the ammonia gas neutralization reaction, a molar ratio of the ammonia gas to the sucrose-6-carboxylate is in a range of 0.5 to 6.0.

9. The post-treatment method according to claim 1, wherein in the acid value adjustment reaction, the predetermined acidity range is in a range of 4.0 to 7.5.

10. The post-treatment method according to claim 1, wherein in the acid value adjustment reaction, the acid is selected from the group consisting of hydrochloric acid and acetic acid.

11. The post-treatment method according claim 2, wherein in the preliminary neutralization reaction, a molar ratio of the ammonia water or the water to the sucrose-6-carboxylate is in a range of 0.5 to 2.5.

12. The post-treatment method according claim 3, wherein in the preliminary neutralization reaction, a molar ratio of the ammonia water or the water to the sucrose-6-carboxylate is in a range 0.5 to 2.5.

13. The post-treatment method according to claim 2, wherein in the ammonia gas neutralization reaction, the predetermined temperature is in a range of 40° C. to 70° C.; and
the predetermined alkalinity range is in a range of 8.0 to 8.5.

14. The post-treatment method according to claim 3, wherein in the ammonia gas neutralization reaction, the predetermined temperature is in a range of 40° C. to 70° C.; and
the predetermined alkalinity range is in a range of 8.0 to 8.5.

15. The post-treatment method according to claim 2, wherein in the ammonia gas neutralization reaction, the reaction temperature is in a range of 20° C. to 50° C.; and
the predetermined reaction time is in a range of 2 h to 6 h.

16. The post-treatment method according to claim 3, wherein in the ammonia gas neutralization reaction, the reaction temperature is in a range of 20° C. to 50° C.; and
the predetermined reaction time is in a range of 2 h to 6 h.

17. The post-treatment method according to claim 2, wherein in the ammonia gas neutralization reaction, a molar ratio of the ammonia gas to the sucrose-6-carboxylate is in a range of 2.0 to 4.0.

18. The post-treatment method according to claim 3, wherein in the ammonia gas neutralization reaction, a molar ratio of the ammonia gas to the sucrose-6-carboxylate is in a range of 2.0 to 4.0.

19. The post-treatment method according to claim 2, wherein in the acid value adjustment reaction, the predetermined acidity range is in a range of 5.5 to 7.0.

20. The post-treatment method according to claim 3, wherein in the acid value adjustment reaction, the predetermined acidity range is in a range of 5.5 to 7.0.

* * * * *